United States Patent [19]

Johnson

[11] 4,374,135

[45] Feb. 15, 1983

[54] COMPOSITIONS CONTAINING ANOREXIGENIC COMPOUNDS AND METHODS FOR REGULATING THE FEED INTAKE OF HOMOTHERMIC ANIMALS

[75] Inventor: Melvin C. Johnson, East Brunswick, N.J.

[73] Assignee: American Cyanamid Company, Stamford, Conn.

[21] Appl. No.: 213,287

[22] Filed: Dec. 5, 1980

[51] Int. Cl.³ ............... A61K 31/505; A61K 31/33; A61K 31/15
[52] U.S. Cl. ............................ 424/251; 424/244; 424/327
[58] Field of Search .................... 424/244, 251

[56] References Cited

U.S. PATENT DOCUMENTS

| | | | |
|---|---|---|---|
| 3,878,201 | 4/1975 | Tomcufcik | 424/244 |
| 3,931,152 | 1/1976 | Tomcufcik et al. | 424/244 |
| 4,087,525 | 5/1978 | Lovell | 424/244 |
| 4,152,436 | 5/1979 | Drabb | 424/244 |
| 4,163,102 | 7/1979 | Lovell | 424/251 |
| 4,191,768 | 3/1980 | Drabb et al. | 424/251 |
| 4,213,988 | 7/1980 | Lovell | 424/251 |

*Primary Examiner*—Douglas W. Robinson
*Attorney, Agent, or Firm*—Thomas J. Monahan

[57] ABSTRACT

There are provided novel compositions and methods for the control of the appetite by controlling and maintaining the body weight of homothermic animals while administering to the same an appetite suppressing amount of an amidino hydrazone compound.

13 Claims, No Drawings

COMPOSITIONS CONTAINING ANOREXIGENIC COMPOUNDS AND METHODS FOR REGULATING THE FEED INTAKE OF HOMOTHERMIC ANIMALS

The present invention is directed to a method for the control and maintenance of body weight of homothermic animals. More particularly, it relates to a method for regulating the food intake of homothermic animals utilizing an anorexigenic compound. Still more particularly, the invention is concerned with the use of an anorexigenic compound, hereinbelow defined, by administering to homothermic animals on a daily or some other suitably recurring basis, an appetite suppressing or anorexigenic amount of such compound.

In general there is contemplated an anorexigenic compound having the formula:

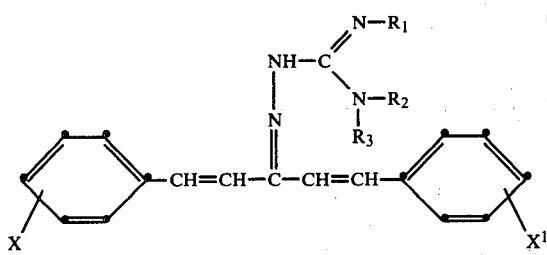

wherein X and $X^1$ each represent hydrogen, halogen, $CF_3$, $C_1$–$C_4$ alkyl, $C_1$–$C_4$ alkoxy or $C_1$–$C_4$ alkylthio; $R_1$ and $R_2$ each represent hydrogen or $C_1$–$C_4$ alkyl and when taken together, they represent an unsubstituted alkylene group of 2 to 6 carbon atoms, a monomethyl or monophenyl substituted alkylene group of 2 to 4 carbon atoms, a dimethyl alkylene group of 2 to 4 carbon atoms, or 1,2-cyclohexylene; $R_3$ is hydrogen or $C_1$–$C_4$ alkyl; and the acid addition salts thereof.

Preferred compounds have the above structure wherein X and $X^1$ represent the same substituent, and the substituent is hydrogen, Br, Cl, $CF_3$, $CH_3$, $CH_3O$ or $CH_3S$; $R_1$ and $R_2$ each represent hydrogen, $C_1$–$C_3$ alkyl, $C_2$–$C_6$ alkylene, or methyl, dimethyl or phenyl substituted $C_2$–$C_4$ alkylene; $R_3$ is hydrogen; and the acid addition salts thereof, preferably the hydrochloride, hydrobromide or hydriodide.

Most preferred compounds are those having the structures:

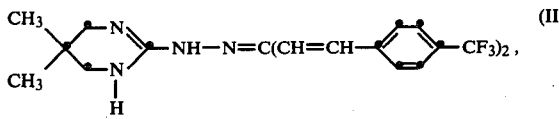

1,5-bis($\alpha,\alpha,\alpha$-trifluoro-p-tolyl)-1,4-pentadien-3-one, (1,4,5,6-tetrahydro-5,5-dimethyl-2-pyrimidinyl)hydrazone.

or

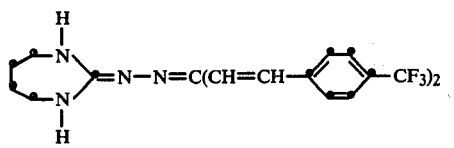

1,5-bis($\alpha,\alpha,\alpha$-trifluoro-p-tolyl)-1,4-pentadien-3-one(E,E)-azine with hexahydro-2H-1,3-diazepin-2-one.

or

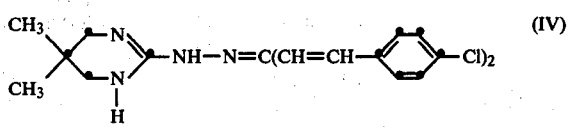

1,5-bis(p-chlorophenyl-1,4-pentadien-3-one (1,4,5,6-tetrahydro-5,5-dimethyl)hydrazone.

or

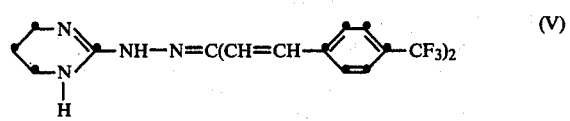

1,5-bis($\alpha,\alpha,\alpha$-trifluoro-p-tolyl)-1,4-pentadien-3-one 1,4,5,6-tetrahydro-2-pyrimidinylhydrazone.

It is common practice to feed domesticated homothermic animals, and especially companion animals, such as dogs and cats, by providing them with feed and water ad libitum. Under such circumstances, said animals can be expected to gain weight in most cases quite rapidly. In addition, and especially in the case of the companion animals, these are often being rewarded with various tasty and high caloric tidbits by their owners, thus further contributing to the weight problem of said animals. To insure at least weight maintenance, it is desirable to control and/or suppress the appetite of certain domestic and especially of companion animals, such as dogs and cats, in order to maintain their body weight at an adequate, preferably optimum, level to protect said animals from becoming obese and ultimately fall victim to diseases induced by obesity.

It has now been found that, by the method of the present invention, the appetite of domestic animals and especially companion animals, such as dogs and cats, can be controlled by administering to said animals on a daily basis or some other, suitable timed interval, an appetite suppressing amount of a compound of formula (I), hereinabove defined.

These compounds may be administered in or with said animals' feed in amounts ranging from about 5 ppm to about 800 ppm and, preferably, 30 ppm to 200 ppm of feed per day. Said compounds may also be given orally as pills, capsules, boluses, pastes and the like in amounts ranging from about 3 mg to 150 mg/kg body weight and, preferably, 12 to 30 mg/kg body weight per day, formulated, if necessary or desired, with pharmaceutically acceptable, inert diluents, binders, lubricants, antistatic agents, surfactants and the like. Formula (I) compounds may also be administered as timed release implants, formulated so as to release the compounds at an approximately uniform rate over a prolonged period of time. For short term treatment the compounds may also be administered as subcutaneous, intramuscular, intraperitoneal or intravenous injection in amounts of from about 3 mg to about 30 mg/kg body weight and preferably 9 mg to 12 mg/kg body weight.

The compounds represented by formula (I) above may also be used to good advantage to control the appetite and, therefore, the weight of animals kept in zoos and other confined quarters, where, although the amount of feed consumed by said animals is usually controlled, the animals, however, are restricted in their movement, and thus as a general rule, do not have a sufficient amount of exercise and thus tend to become obese.

Another, quite interesting use of these compounds is to incorporate them into baits and/or bait blocks and make these available and accessible to woodchucks where these are present in numbers sufficiently large to represent a threat to crops. By acting as an appetite suppressant, crop damage by foraging wood chucks may be significantly reduced.

It is recognized, of course, that such techniques may generally be applicable to minimize crop damage and/or losses by controlling the appetite of foraging wild animals.

The following non-limiting examples serve to further illustrate the invention of the present application.

EXAMPLE 1

Evaluation of the Anorexigenic Effects of the Compounds of the Present Invention in Rats Weanling rats, 29 days old are housed in wire cages, one rate per cage, six rats, three of each sex, are allotted to each treatment.

All rats are fed a standard rodent laboratory chow (description appended to Example) for eight days prior to allottment to treatment. The rats are then offered test feeds and water ad libitum for 27 days. The compounds are incorporated in said feed at three levels, namely (a) 50, (b) 200 and (c) 800 ppm levels, respectively. The animals are weighed weekly and feed consumption measured for each period. The data are averaged and summarized in Table I below.

Composition of Rodent Laboratory Chow

Crude protein, minimum 23.0%
Crude fat, minimum 4.5%
Crude fiber, maximum 6.0%
Ash, maximum 8.0%
Added minerals, maximum 2.5%

Ground extruded corn, soybean meal, ground oats groats, dried beet pulp, wheat germ meal, fish meal, brewers' dried yeast, dehydrated alfalfa meal, cane molasses, dried milk products, meat and bone meal, wheat middlings, animal fat preserved with BHA, calcium carbonate, dicalcium phosphate, salt, animal liver meal, calcium iodate, vitamin $B_{12}$ supplement, methionate hydroxy analogue calcium, calcium pantothenate, choline chloride, folic acid, riboflavin supplement, thiamin, niacin, pyridoxine hydrochloride, ferrous sulfate, vitamin A supplement, D-activated animal sterol, vitamin E supplement, iron oxide, manganous oxide, cobalt carbonate, copper oxide, zinc oxide.

EXAMPLE 2

Evaluation of the Anorexigenic Effects of a Compound of the Invention in Chickens Day old chicks are randomly distributed in pens, five males and five females per pen. Four pens are allotted to each treatment and a total of twelve pens are used as controls.

Test feeds are made up from broiler ration No. 453 and drug, at the drug levels indicated in Table II and III below. The control groups receive the same broiler

TABLE I

Evaluation of the Anorexigenic Effects of the Compounds of the Invention in Rats, 27-Day Data, Averaged

| Compound | Feed Level (ppm) | Weight Gain in Grams | Feed Consumed in Grams | Feed/Gain Ratio | Percent Weight Loss (−) or Gain (+) over Controls |
|---|---|---|---|---|---|
| Control | — | 149.8 | 495.9 | 3.3104 | — |
| (CH₃)₂C(N-NH)–NH–N=C(CH=CH–pyridyl–CF₃)₂ | 50 | 145.8 | 488.9 | 3.3532 | −2.67 |
|  | 200 | 117.8 | 423.1 | 3.5917 | −21.36 |
|  | 800 | 6.6 | 151.5 | −22.9545 | −104.41 |
| (pyrazole)=N–N=C(CH=CH–pyridyl–CF₃)₂ | 50 | 152.5 | 492.9 | 3.2321 | +1.80 |
|  | 200 | 140.9 | 447.5 | 3.1760 | −5.94 |
|  | 800 | 12.3 | 200.2 | 16.2764 | −91.79 |
| (CH₃)₂C(N-NH)–NH–N=C(CH=CH–pyridyl–Cl)₂ | 50 | 144.4 | 496.3 | 3.4370 | −3.60 |
|  | 200 | 136.9 | 464.6 | 3.3937 | −8.61 |
|  | 800 | 20.5 | 225.7 | 11.0098 | −86.31 |
| (pyrazole)–NH–N=C(CH=CH–pyridyl–CF₃)₂ | 50 | 114.0 | 483.3 | 4.2395 | −23.90 |
|  | 200 | 137.3 | 441.6 | 3.2163 | −8.34 |
|  | 800 | 28.8 | 231.2 | 8.0278 | −80.77 | ration without drug. Feed and water are offered to controls and treatment groups ad libitum for a period of 27 days. The birds are weighed at 14 and at 27 days and feed consumption measured for each period. The data are averaged and summarized in Tables II and III below.

TABLE II

Evaluation of the Anorexigenic Effects of a Compound of the Invention in Chickens. Fourteen-Day Data, Averaged (Day 1 to 14).

| Compound | Feed Level (ppm) | Weight Gain in Grams | Feed Consumed in Grams | Feed/Gain Ratio | Percent Weight Loss (−) or Gain (+) over Controls |
|---|---|---|---|---|---|
| Control | — | 211.6 | 309.0 | 1.461 | — |
| $CH_3$\\\\N—NH—N=C(CH=CH—⌬—$CF_3$)$_2$ / $CH_3$/N(H) | 5 | 212.0 | 309.6 | 1.467 | +0.19 |
| | 10 | 215.7 | 309.2 | 1.433 | +1.94 |
| | 20 | 216.3 | 314.4 | 1.456 | +2.22 |
| | 80 | 214.7 | 314.1 | 1.464 | +1.46 |
| | 160 | 200.8 | 299.8 | 1.493 | −5.10 |
| | 320 | 189.7 | 284.6 | 1.501 | −10.35 |
| | 640 | 176.7 | 280.6 | 1.590 | −16.49 |

TABLE III

Evaluation of the Anorexigenic Effects of a Compound of the Invention in Chickens. Fourteen-Day Data, Averaged (Day 14 to 27).

| Compound | Feed Level (ppm) | Weight Gain in Grams | Feed Consumed in Grams | Feed/Gain Ratio | Percent Weight Loss (−) or Gain (+) over Controls |
|---|---|---|---|---|---|
| Control | — | 472.0 | 731.7 | 1.548 | — |
| $CH_3$\\\\N—NH—N=C(CH=CH—⌬—$CF_3$)$_2$ / $CH_3$/N(H) | 5 | 484.2 | 745.1 | 1.546 | +2.58 |
| | 10 | 467.4 | 731.5 | 1.563 | −0.97 |
| | 20 | 497.1 | 764.1 | 1.543 | +5.32 |
| | 80 | 485.6 | 756.7 | 1.558 | +2.88 |
| | 160 | 452.2 | 734.6 | 1.632 | −4.19 |
| | 320 | 459.1 | 709.7 | 1.560 | −2.73 |
| | 640 | 450.7 | 699.6 | 1.553 | −4.51 |

| Broiler Ration No. 453 | |
|---|---|
| Component | Percent by Weight |
| Ground yellow corn | 53.45 |
| Soybean oil meal (49%) | 28.00 |
| Menhaden fish meal (60%) | 5.00 |
| Corn Gluten meal (60%) | 5.00 |
| Dehydrated Alfalfa meal (17%) | 2.00 |
| Stabilized fat | 4.00 |
| Dicalcium phosphate | 1.20 |
| Ground limestone | 0.50 |
| Sodium chloride | 0.30 |
| Trace Minerals mixture* | 0.05 |
| Vitamin premix** | 0.50 |
| | 100.00 |

| *Trace Mineral Mixture | | 1 lb/ton furnishes |
|---|---|---|
| Manganese | 12.50% | 62.5 ppm |
| Iron | 6.00 | 30.0 |
| Zinc | 5.00 | 25.0 |
| Copper | 0.65 | 3.25 |
| Iodine | 0.355 | 1.75 |
| Cobalt | 0.25 | 1.25 |
| Calcium min. | 15.30 | |
| Calcium max. | 18.35 | |

| **Vitamin Premix for 1-ton | Weight in gram |
|---|---|
| DL Methionine | 453.6 |
| BHT (Butylated Hydroxy toluene) | 113.6 |
| Vitamin A (30,000 mcg/g) | 100.0 |
| Vitamin $D_3$ (200,000 mcg/g) | 5.0 |
| Vitamin E (20,000 mcg/lb) | 45.4 |
| Riboflavin | 4.0 |
| Niacinamide | 25.0 |
| Calcium Pantothenate | 8.0 |

| -continued | |
|---|---|
| Broiler Ration No. 453 | |
| Vitamin K (menadione) | 1.0 |
| Parvo (10%), folic acid | 13.0 |
| Choline Chloride (50%) | 908.0 |
| Proferm (20 mg/lb), $B_{12}$ | 227.0 |
| Corn oil | 50.0 |
| Fine ground corn | 2,582.4 |
| | 4,536.0 |

I claim:

1. A method for reducing the appetite of animals comprising homothermic zoo animals, companion animals and rodents which comprises administering to said animals orally or parenterally an appetite suppressing amount of a compound selected from the group consisting of 1,5-bis($\alpha,\alpha,\alpha$-trifluoro-p-tolyl)-1,4-pentadien-3-one, (1,4,5-6-tetrahydro-5,5-dimethyl-2-pyrimidinyl)-hydrazone; 1,5-bis($\alpha,\alpha,\alpha$-trifluoro-p-tolyl)-1,4-pentadien-3-one-(E,E)-azine with hexahydro-2H-1,3-diazepin-2-one; 1,5-bis(p-chlorophenyl)-1,4-pentadien-3-one, (1,4,5,6-tetrahydro-5,5-dimethyl-2-pyrimidinyl)hydrazone; 1,5-bis($\alpha,\alpha,\alpha$-trifluoro-p-tolyl)-1,4-pentadien-3-one, (1,4,5,6-tetrahydro-2-pyrimidinyl)hydrazone; and acid addition salts thereof.

2. The method according to claim 1, wherein said compound is administered in or with the feed of said animals at a rate of 30 to 200 ppm.

3. The method according to claim 1, wherein said compound is administered orally to said animals at a rate of from 12 to 30 mg/kg body weight daily.

4. The method according to claim 1, wherein said compound is 1,5-bis($\alpha,\alpha,\alpha$-trifluoro-p-tolyl)-1,4-pentadien-3-one, (1,4,5,6-tetrahydro-5,5-dimethyl-2-pyrimidinyl)hydrazone.

5. The method according to claim 1, wherein said compound is 1,5-bis(α,α,α-trifluoro-p-tolyl)-1,4-pentadien-3-one-(E,E)-azine with hexahydro-2H-1,3-diazepin-2-one.

6. The method according to claim 1, wherein said compound is 1,5-bis(p-chlorophenyl)-1,4-pentadien-3-one (1,4,5,6-tetrahydro-5,5-dimethyl-2-pyrimidinyl)hydrazone.

7. The method according to claim 1, wherein said compound is 1,5-bis(α,α,α-trifluoro-p-tolyl)-1,4-pentadien-3-one 1,4,5,6-tetrahydro-2-pyrimidinylhydrazone.

8. The method according to claim 1, wherein said animals are dogs and cats.

9. The method according to claim 1, wherein said animals are rats, mice or woodchucks.

10. The method to minimize losses of fresh and harvested agricultural products due to predation by rodents or homothermic foraging, wild, pest animals comprising: providing said animals with food baits containing an appetite-suppressing amount of: 1,5-bis(α,α,α-trifluoro-p-tolyl)-1,4-pentadien-3-one, (1,4,5,6-tetrahydro-5,5-dimethyl-2-pyrimidinyl)hydrazone; 1,5-bis(α,α,α-trifluoro-p-tolyl)-1,4-pentadien-3-one-(E,E)-azine with hexahydro-2H-1,3-diazepin-2-one; 1,5-bis(p-chlorophenyl)-1,4-pentadien-3-one, (1,4,5,6-tetrahydro-5,5-dimethyl-2-pyrimidinyl)hydrazone; or 1,5-bis(α,α,α-trifluoro-p-tolyl)-1,4-pentadien-3-one, (1,4,5,6-tetrahydro-2-pyrimidinyl)hydrazone; and the acid addition salts thereof.

11. An anorexigenic animal feed composition effective for controlling the weight of homothermic zoo animals, companion animals and rodents comprising: an edible animal feed stuff containing from 5 to 800 ppm of an appetite-suppressing amount of 1,5-bis(α,α,α-trifluoro-p-tolyl)-1,4-pentadien-3-one, (1,4,5,6-tetrahydro-5,5-dimethyl-2-pyramidinyl)hydrazone; 1,5-bis(α,α,α-trifluoro-p-tolyl)-1,4-pentadien-3-one-(E,E)-azine with hexahydro-2H-1,3-diazepin-2-one; 1,5-bis(p-chlorophenyl)-1,4-pentadien-3-one, (1,4,5,6-tetrahydro-5,5-dimethyl-2-pyrimidinyl)hydrazone; or 1,5-bis(α,α,α-trifluoro-p-tolyl)-1,4-pentadien-3-one, (1,4,5,6-tetrahydro-2-pyrimidinyl)hydrazone; and the acid addition salts thereof.

12. The anorexigenic animal feed composition according to claim 11 wherein said feed is a pet or zoo animals feed containing from 30 ppm to 200 ppm of the amidohydrazone compound.

13. The anorexigenic animal feed composition according to claim 11 wherein said feed is a bait for rodent and pest animals containing from about 500 ppm to 800 ppm.

* * * * *